United States Patent [19]

Rasberger

[11] 4,301,061
[45] Nov. 17, 1981

[54] DIBENZODIOXAPHOSPHEPINES AND STABILIZED POLYMERS

[75] Inventor: Michael Rasberger, Riehen, Switzerland

[73] Assignee: Ciba-Geigy Corporation, Ardsley, N.Y.

[21] Appl. No.: 198,075

[22] Filed: Oct. 17, 1980

Related U.S. Application Data

[63] Continuation-in-part of Ser. No. 39,701, May 18, 1979.

[30] Foreign Application Priority Data

May 18, 1978 [CH] Switzerland .................... 5390/78

[51] Int. Cl.³ ........................... C07F 9/65; C08K 5/53
[52] U.S. Cl. .................... 260/45.8 N; 260/45.8 NE; 260/239 B
[58] Field of Search ................. 544/157, 337; 546/21, 546/22; 548/111; 260/399, 403, 923, 927 R, 936, 326.61, 239 B, 45.9 NP, 45.8 N, 45.8 NE

[56] References Cited

U.S. PATENT DOCUMENTS 3,993,655 11/1976 Rasberger et al. .

FOREIGN PATENT DOCUMENTS 179918 2/1966 U.S.S.R. .

OTHER PUBLICATIONS

P. A. Kirpichnikov et al., CA, 73, 15657a (1970).
L. V. Verizhnikov et al., CA, 75, 130242q (1971).
L. Anschutz et al., Chem. Ber., 89, 1119 (1956).

N. A. Mukmeneva et al., CA, 82, 140926z (1975).
L. V. Verizhnikov et al., CA, 68, 12597s (1968).

Primary Examiner—Henry R. Jiles
Assistant Examiner—R. W. Ramsuer
Attorney, Agent, or Firm—Luther A. R. Hall

[57] ABSTRACT

Compounds of the formula I

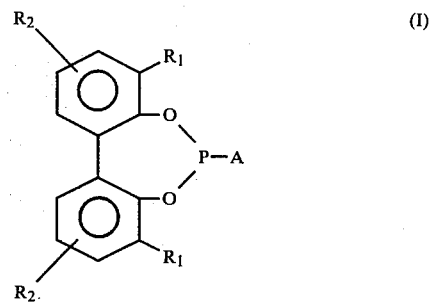

wherein
$R_1$ is $C_1$–$C_{18}$ alkyl,
$R_2$ is hydrogen or $C_1$–$C_{18}$ alkyl, and
A is a substituted primary or secondary aliphatic or alicyclic, aromatic or araliphatic amine, in which the substituents are identical or different, a heterocyclic amine or a hydrazine derivative are disclosed.

The compounds are stabilizers for organic materials. Stabilized organic materials are also disclosed.

3 Claims, No Drawings

DIBENZODIOXAPHOSPHEPINES AND STABILIZED POLYMERS

This is a continuation-in-part application of application Ser. No. 039,701 filed May 18, 1979.

The present invention relates to new N-substituted 6-amino-dibenz[d,f][1,3,2]dioxaphosphepines, to the production thereof, to their use as stabilisers for organic material, and to the organic material stabilised by means of these compounds.

Phosphonites are known to be stabilisers. These phosphonites do not however meet in every respect the high requirements that a stabiliser has to meet, particularly in respect of storage stability, water absorption, sensitivity to hydrolysis, processing stabilisation, colour behaviour, volatility, migration behaviour, compatibility and improved stability to light.

It was the object of the invention to provide stabilisers which do not have these disadvantages, or have them to a lesser extent.

The present invention relates to N-substituted 6-amino-dibenz[d,f][1,3,2]dioxaphosphepines of the formula (I)

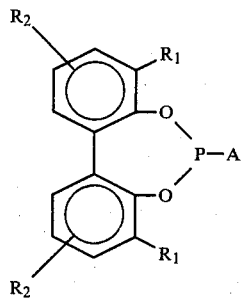

wherein
$R_1$ is $C_1$–$C_{18}$ alkyl,
$R_2$ is hydrogen or $C_1$–$C_{18}$ alkyl, and
A is a substituted primary or secondary aliphatic or alicyclic, aromatic or araliphatic amine, in which the substituents are identical or different, a heterocyclic amine or a hydrazine derivative.

As $C_1$–$C_{18}$ alkyl, $R_1$ and $R_2$ are in particular straight-chain or branched-chain alkyl having 1–8 C atoms, for example methyl, ethyl, n-propyl, iso-propyl, sec-butyl, tert-butyl, tert-pentyl, n-octyl, 2-ethylhexyl or 1,1,3,3-tetramethylbutyl. $R_1$ is preferably α-branched. In particularly preferred compounds, $R_1$ and $R_2$ have the same meaning.

The radicals $R_2$ are preferably in the 1- and 11-position, but especially in the 2- and 10-position.

A is a substituted primary or secondary amine in which the substituents are identical or different, which amine can contain up to six primary and/or secondary amino groups. Preferred compounds are those in which all primary or secondary amine nitrogen atoms occurring in the molecule are substituted by a group of the formula II

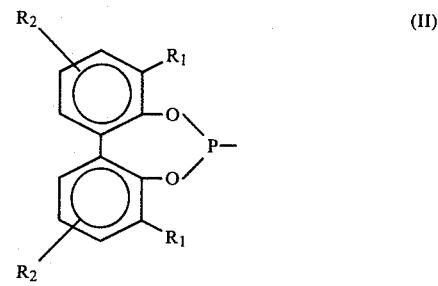

The symbols $R_1$ and $R_2$ in the formula II have the meanings given above.

Of interest in particular are secondary amines, and especially branched-chain amines.

Preferred amines A are therefore those of the formula III

wherein
$R_3$ is hydrogen, $C_1$–$C_{22}$ alkyl, $C_2$–$C_{21}$ oxa- or thiaalkyl, $C_3$–$C_{18}$ alkenyl, $C_3$–$C_{18}$ alkynyl, $C_2$–$C_6$ hydroxyalkyl, $C_3$–$C_{24}$ alkoxycarbonylalkyl, $C_5$–$C_{12}$ cycloalkyl, $C_6$–$C_{14}$ aryl, $C_7$–$C_{15}$ alkaryl, $C_7$–$C_{15}$ aralkyl, a substituted or unsubstituted $C_5$–$C_{17}$ piperidin-4-yl group, or a group of the formula II in which $R_1$ and $R_2$ have the meanings given above, and
$R_4$ is $C_1$–$C_{22}$ alkyl, $C_2$–$C_{21}$ oxa- or thiaalkyl, $C_3$–$C_{18}$ alkenyl, $C_3$–$C_{18}$ alkynyl, $C_2$–$C_6$ hydroxyalkyl, $C_3$–$C_{24}$ alkoxycarbonylalkyl, $C_5$–$C_{12}$ cycloalkyl, $C_6$–$C_{14}$ aryl, $C_7$–$C_{15}$ alkaryl, $C_7$–$C_{15}$ aralkyl, a substituted or unsubstituted $C_5$–$C_{17}$ piperidin-4-yl group, a group of the formula IV

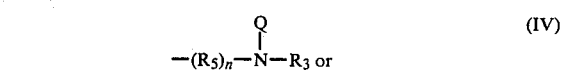

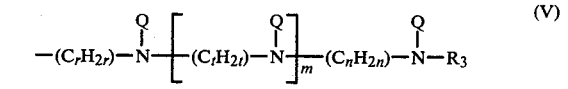

wherein
$R_3$ has the meaning given above,
n is 0 or 1,
$R_5$ is $C_2$–$C_{22}$ alkylene, $C_4$–$C_{22}$ alkenylene, $C_4$–$C_{22}$ alkynylene or $C_5$–$C_9$ cycloalkylene, each of which can be interrupted with one or two oxygen or sulfur atoms, or $R_5$ is a group of the formula VI

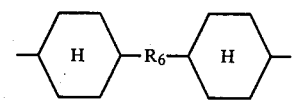

in which $R_6$ is —O—, —S— or —($R_7$)C($R_8$)—, wherein $R_7$ and $R_8$ independently of one another are hydrogen or $C_1$–$C_8$ alkyl, or $R_7$ and $R_8$ together with the C atom to which they are attached form $C_5$–$C_{12}$ cycloalkyl, or $R_7$ and $R_8$ together are 1,4-cyclohexylenedimethylene or 1,3,3-trimethylcyclohexylene-1,5, or $R_5$ is also phenylene, biphenylene or a group of the formula

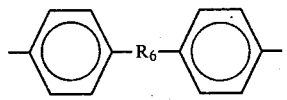

wherein
$R_6$ has the meaning given above, and r, t and n independently of one another are 2, 3, 4, 5 or 6,
m is 0, 1, 2 or 3,
Q is a group of the formula II, wherein $R_1$ and $R_2$ have the meanings given above, or
$R_3$ and $R_4$ together with the N atom to which they are attached are also substituted pyrrolidine, oxazolidine, piperidine or morpholine, or $R_3$ and $R_4$ together form the radical —CH$_2$—CH$_2$—N(Q)—CH$_2$—CH$_2$— wherein Q has the meaning given above.

If $R_3$ and $R_4$ are each $C_1$–$C_{22}$ alkyl, they can be methyl, ethyl, n-propyl, isopropyl, n-butyl, sec-butyl, tert-butyl, n-pentyl, n-hexyl, isohexyl, n-octyl, 1,1,3,3-tetramethylbutyl, n-nonyl, decyl, dodecyl, tetradecyl, hexadecyl, octadecyl, eicosyl or docosyl. As alkyl groups, $R_3$ and $R_4$ preferably contain 1–18 C atoms, with $R_3$ containing in particular 1–12 C atoms and $R_4$ in particular 1–4 C atoms. As $C_2$–$C_{21}$, especially $C_4$–$C_{21}$, oxa- or thiaalkyl, $R_3$ and $R_4$ are preferably alkoxy- or alkylthiopropyl, such as butoxypropyl, dodecylthiopropyl, octyloxypropyl or octadecyloxypropyl, As $C_3$–$C_{18}$ alkenyl, $R_3$ and $R_4$ are for example allyl, methallyl, n-hex-3-enyl, n-oct-4-enyl or n-undec-10-enyl. Allyl and methallyl are preferred, and especially allyl.

As $C_3$–$C_{18}$ alkynyl, $R_3$ and $R_4$ are for example propargyl, n-but-1-ynyl, n-but-2-ynyl or n-hex-1-ynyl. Alkynyl groups having 3 or 4 C atoms and particularly propargyl are preferred.

If $R_3$ and $R_4$ are each hydroxyalkyl having 1–6 C atoms, they can be 2-hydroxypropyl, 2-hydroxyethyl, 3-hydroxypropyl, 4-hydroxybutyl or 6-hydroxyhexyl.

If $R_3$ and $R_4$ are each $C_3$–$C_{24}$ alkoxycarbonylalkyl, preferably $C_3$–$C_{24}$ alkoxycarbonylmethyl or -ethyl and in particular $C_3$–$C_{14}$ alkoxycarbonylmethyl or $C_3$–$C_{15}$ alkoxycarbonylethyl, they can be for example methoxycarbonylmethyl, ethoxymethyl, methoxycarbonylethyl, octoxycarbonylmethyl, octoxycarbonylbutyl, dodecyloxycarbonylethyl or octadecyloxycarbonylethyl.

As $C_5$–$C_{12}$, preferably $C_5$–$C_8$ and especially $C_6$, cycloalkyl, $R_3$ and $R_4$ are for example cyclopentyl, cyclohexyl, cycloheptyl, cyclooctyl, cyclononyl or cyclododecyl.

As $C_6$–$C_{14}$ aryl, $R_3$ and $R_4$ are for example phenyl, α-naphthyl, β-naphthyl or phenanthryl. Phenyl groups are preferred.

If $R_3$ and $R_4$ are aralkyl having $C_7$–$C_{15}$ C atoms, they are for example benzyl, α-phenylethyl, α,α-dimethylbenzyl or 2-phenylethyl, preferably benzyl.

As $C_7$–$C_{15}$ alkaryl groups, $R_3$ and $R_4$ can be for example tolyl, 2,6-dimethylphenyl, 2,6-diethylphenyl, 2,4,6-triisopropylphenyl or 4-tert-butylphenyl.

If $R_3$ and $R_4$ are $C_5$–$C_{17}$ piperidin-4-yl groups, they can be for example unsubstituted piperidin-4-yl, or the piperidine can be substituted by up to 5 alkyl groups, preferably by methyl or ethyl groups. Preferred substitution positions are the 2- and 6-positions in the piperidine ring. They can also be 3,3,5-trimethyl-8-ethoxy-bicyclo[4,4,0]dec-2-yl.

$R_3$ and $R_4$ can therefore form piperidin-4-yl groups of the following structure:

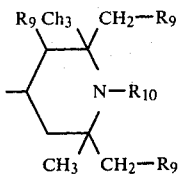

wherein $R_9$ is hydrogen or methyl, and $R_{10}$ is hydrogen, oxyl, $C_1$–$C_{18}$ alkyl, $C_3$–$C_8$ alkenyl, $C_3$–$C_6$ alkynyl, $C_7$–$C_{12}$ aralkyl, $C_2$–$C_{21}$ alkoxyalkyl, an aliphatic acyl group having 1–4 C atoms, or a group —CH$_2$COOR$_{11}$ wherein $R_{11}$ is $C_1$–$C_{12}$ alkyl, $C_3$–$C_8$ alkenyl, phenyl, $C_7$–$C_8$ aralkyl or cyclohexyl.

Very particularly preferred piperidin-4-yl groups are those wherein $R_9$ is hydrogen, and $R_{10}$ is hydrogen, methyl or acetyl.

The preferred meaning of $R_9$ is hydrogen.

As $C_1$–$C_{18}$ alkyl, $R_{10}$ is for example methyl, ethyl, n-propyl, n-butyl, n-pentyl, n-octyl, n-decyl, n-dodecyl or actadecyl. Preferred alkyl groups are those having 1 to 12 C atoms, especially those having 1 to 8 C atoms, in particular those having 1 to 4 C atoms, and above all methyl.

As $C_3$–$C_8$ alkenyl, $R_{10}$ is for example allyl, 3-methyl-2-butenyl, 2-butenyl, 2-hexenyl or 2-octenyl, especially allyl.

As $C_3$–$C_6$ alkynyl, $R_{10}$ is for example propargyl.

As $C_7$–$C_{12}$ aralkyl, $R_{10}$ is for example benzyl, β-phenylethyl or 4-tert-butyl-benzyl, preferably benzyl.

If $R_{10}$ is $C_2$–$C_{21}$ alkoxyalkyl, the alkyl moiety can contain 1 to 3 C atoms, and the alkoxy moiety can consist of 1 to 18 C atoms, such as in methoxymethyl, ethoxymethyl, 2-methoxyethyl, 2-ethoxyethyl, 2-n-butoxyethyl, 3-n-butoxypropyl, 2-octoxyethyl or 2-octadecyloxyethyl. To be particularly mentioned are compounds in which $R_{10}$ is an alkoxyalkyl group having 2 to 6 C atoms.

As an aliphatic acyl group having 1 to 4 C atoms, $R_{10}$ is for example formyl, acetyl, acryloyl or crotonyl, especially acetyl.

If $R_{10}$ is the group —CH$_2$COOR$_{11}$, $R_{11}$ as $C_1$–$C_{12}$ alkyl is for example methyl, ethyl, isopropyl, n-butyl, isobutyl, tert-butyl, isopentyl, n-octyl or n-dodecyl. Preferably $R_{11}$ is $C_1$–$C_4$ alkyl. As $C_3$–$C_8$ alkenyl, $R_{11}$ is for example allyl, 2-butenyl or 2-hexenyl. As $C_7$–$C_8$ aralkyl, $R_{11}$ is for example benzyl or α-phenylethyl.

If $R_3$ is a group of the formula II, this group preferably has the same substitution as the dibenz[d,f][1,3,2]dioxaphosphepin-6-yl group already present in the molecule.

If $R_3$ and $R_4$ with the N atom to which they are attached form a pyrrolidine, oxazolidine, piperidine or morpholine ring, these heterocycles can be substituted by up to five methyl or ethyl groups. These ring systems are preferably unsubstituted.

The symbol n can be 0 or preferably 1.

As $C_2$–$C_{22}$ alkylene, preferably $C_2$–$C_9$ and particularly $C_2$–$C_6$ alkylene, $R_5$ can be for example dimethylene, trimethylene, tetramethylene, hexamethylene, octamethylene, nonamethylene, 2,2,4-trimethylhexamethylene, decamethylene, dodecamethylene, octadecamethyl or docosamethylene. If the alkylene groups are interrupted by —O— or —S—, they can be 2-thiapropylene-1,3, 3-thiapentylene-1,5,4-oxaheptamethylene or 3,6-dioxaoctylene-1,8.

If $R_5$ is $C_4$-$C_{22}$ alkenylene or alkynylene, it is for example 2-butenylene-1,4, 2-butynylene-1,4, 2,4-hexadiinylene-1, or propenylene-1,3.

As $C_5$-$C_9$ cycloalkylene, $R_5$ is for example 1,2-cyclopentylene, 1,2-cyclohexylene, 1,3-cyclohexylene, 1,4-cyclohexylene, 1,4-cycloheptylene or 1,2-cyclononylene. As cycloalkylene, $R_5$ preferably has 6 C atoms.

$R_7$ and $R_8$ as $C_1$-$C_8$ alkyl are for example ethyl, n-propyl, isopropyl, n-butyl, n-phenyl, n-hexyl or n-octyl. As alkyl groups, $R_7$ and $R_8$ are preferably however methyl.

With the C atom to which they are attached, $R_7$ and $R_8$ can also form $C_5$-$C_{12}$ cycloalkyl, preferably cyclohexyl. It can be cyclopentyl, cyclohexyl, cycloheptyl, cyclooctyl or cyclododecyl.

Independently of one another, r, t and n are 2, 3, 4, 5 or 6; they are preferably however identical, and are in particular 2 or 3.

m can be 0, 1, 2 or 3. Preferably m is 0 or 1, but particularly 0.

If radicals Q are present in the compounds, these are preferably substituted in the same way as the other dibenz[d,f][1,3,2]dioxaphepin-6-yl groups present in the molecule.

Preferred compounds of the formula I are those wherein
$R_1$ and $R_2$ are each $C_1$-$C_8$ alkyl,
A is a group —N($R_3$)$R_4$ (III), wherein
$R_3$ is hydrogen, $C_1$-$C_{18}$ alkyl, $C_3$-$C_4$ alkenyl, $C_3$-$C_4$ alkynyl, $C_3$-$C_{24}$ alkoxycarbonylmethyl or —ethyl, $C_5$-$C_{12}$ cycloalkyl, phenyl, benzyl, $C_7$-$C_{15}$ alkaryl, a substituted or unsubstituted $C_5$-$C_{17}$ piperidin-4-yl group, or a group of the formula II, wherein $R_1$ and $R_2$ have the meanings given above,
$R_4$ is $C_1$-$C_{18}$ alkyl, $C_3$-$C_4$ alkenyl, $C_3$-$C_4$ alkynyl, $C_3$-$C_{24}$ alkoxycarbonylmethyl or —ethyl, $C_5$-$C_{12}$ cycloalkyl, phenyl, benzyl, $C_7$-$C_{15}$ alkaryl, a substituted or unsubstituted $C_5$-$C_{17}$ piperidin-4-yl group, a group of the formula IV or V, wherein $R_3$ has the meaning given above,
n is 0 or 1,
$R_5$ is $C_2$-$C_9$ alkylene which can be interrupted with one or two oxygen or sulfur atoms, or it is cyclohexylene, or a group of the formula VI, wherein
$R_6$ is —O—, —S— or —($R_7$)C($R_8$)—, wherein
$R_7$ and $R_8$ independently of one another are hydrogen or methyl, or
$R_7$ and $R_8$ together with the C atom to which they are attached form cyclohexylene, or
$R_7$ and $R_8$ together are 1,4-cyclohexylenedimethylene or 1,3,3-trimethyl-cyclohexylene-1,5,
r, t and n are 2 or 3,
m is 0 or 1,
Q is a group of the formula II, wherein $R_1$ and $R_2$ have the meanings given above, or
$R_3$ and $R_4$ together with the N atom to which they are attached form a pyrrolidine, oxozolidine, piperidine or morpholine ring, or
$R_3$ and $R_4$ together are the radical —CH$_2$CH$_2$—N(Q)—CH$_2$CH$_2$—, wherein Q has the meaning given above.

Of interest are compounds of the formula I wherein
$R_1$ is α-branched $C_3$-$C_8$ alkyl,
$R_2$ is $C_1$-$C_8$ alkyl,
A is a group —N($R_3$)$R_4$ (III), wherein
$R_3$ is hydrogen, $C_1$-$C_{18}$ alkyl, allyl, propargyl, $C_3$-$C_{14}$ alkoxycarbonylmethyl, $C_3$-$C_{15}$ alkoxycarbonylethyl or $C_5$-$C_8$ cycloalkyl,
$R_4$ is $C_1$-$C_4$ alkyl, allyl, propargyl, $C_3$-$C_{14}$ alkoxycarbonylmethyl, $C_3$-$C_{15}$ alkoxycarbonylethyl, $C_5$-$C_8$ cycloalkyl, or a group of the formula IV or V, wherein $R_3$ has the meaning given above,
n is 1,
$R_5$ is $C_2$-$C_6$ alkylene,
r, t and n are 2 or 3,
m is 0,
Q is a group of the formula II, wherein $R_1$ and $R_2$ have the meanings given above, or
$R_3$ and $R_4$ together with the C atom to which they are attached form a piperidine or morpholine ring, or
$R_3$ and $R_4$ together are the radical —CH$_2$CH$_2$—N(Q)—CH$_2$CH$_2$— wherein Q has the meaning given above.

Particularly preferred are compounds of the formula I wherein
$R_1$ and $R_2$ are α-branched $C_3$-$C_8$ alkyl,
A is a group —N($R_3$)$R_4$ (III), wherein
$R_3$ is hydrogen, $C_1$-$C_{12}$ alkyl or cyclohexyl,
$R_4$ is $C_1$-$C_4$ alkyl, cyclohexyl, or a group of the formula IV, wherein $R_3$ has the meaning given above, and Q is a group of the formula II, wherein $R_1$ and $R_2$ have the meanings given above,
n is 1,
$R_5$ is $C_2$-$C_6$ alkylene, or
$R_3$ and $R_4$ together with the C atom to which they are attached form a piperidine or morpholine ring, or
$R_3$ and $R_4$ together are the radical —CH$_2$CH$_2$—N(Q)—CH$_2$CH$_2$—, wherein Q has the meaning given above.

Examples of compounds of the formula I are:
(1) 6-(N,N-di-n-octylamino)-2,4,8,10-tetra-tert-butyl-dibenz[d,f][1,3,2]dioxaphosphepine,
(2) 6-(2'-aza-3',3',5'-trimethyl-8'-ethoxy-bicyclo-[4.4.0]dec-2'-yl-2,4,8,10-tetra-tert-octyl-dibenz-[d,f][1,3,2]-dioxaphosphepine,
(3) 6-(N-2',6'-dimethylphenyl-N-cyclohexylamino)-2,10-dimethyl-4,8-di-tert-butyl-dibenz[d,f][1,3,2]-dioxaphosphepine,
(4) 6-(N-cyclododecyl-N-tert-octylamino)-2,4,8,10-tetra-tert-butyl-dibenz[d,f][1,3,2]dioxaphosphepine,
(5) 6-(N-tert-butylamino)-2,4,8,10-tert-butyl-dibenz-[d,f][1,3,2]dioxaphosphepine,
(6) 6-(N-n-octadecylamino)-2,10-dimethyl-4,8-di-tert-butyl-dibenz[d,f][1,3,2]dioxaphosphepine,
(7) 6-(N-cyclododecylamino)-2,4,8,10-tetra-tert-butyl-dibenz[d,f][1,3,2]dioxaphosphepine,
(8) 6-(N-2',6'-dimethylphenylamino)-2,10-dimethyl-4,8-di-tert-octyl-dibenz[d,f][1,3,2]dioxaphosphepine,
(9) 6-(N-p-tert-octylphenyl-N-isopropylamino)-2,4,8,10-tetra-tert-pentyl-dibenz[d,f][1,3,2]-dioxaphosphepine,
(10) 6-(N-cyclohexyl-N-allylamino)-2,4,8,10-tetra-tert-octyl-dibenz[d,f][1,3,2]dioxaphosphepine,
(11) 2,2-bis-[4'-[N-2'',4'',8'',10''-tetra-tert-butyl-dibenz[d,f][1,3,2]dioxaphosphepin-6''-yl)-amino]-cyclohexyl]-propane,
(12) N,N'-bis-(2,4,8,10-tetra-tert-butyl-dibenz[d,f][1,3,2-]dioxaphosphetin-6-yl)-benzidine,
(13) N,N'-bis-(2,4,8,10-tetra-tert-pentyl-dibenz[d,f][1,3,2]dioxaphosphetin-6-yl)-N,N'-dicyclopentylhexamethylene-diamine,
(14) N,N'-bis-(2,4,8,10-tetra-tert-butyl-dibenz[d,f][1,3,2-]dioxaphosphetin-6-yl)-N,N'-di-isopropylhydrazine,

(15) N,N'-bis-(2,10-di-tert-octyl-4,8-di-tert-butyl-dibenz-[d,f][1,3,2]dioxaphosphetin-6-yl)-N,N'-(1'-isopropyl-2-methylpropyl)-ethylenediamine,

(16) N,N'-bis-(2',4',8',10'-tetra-tert-butyl-dibenz[d,f][1,3,2]dioxaphosphepin-6'-yl)-4,9-dioxadodecamethylenediamine,

(17) N,N'-bis-(2,10-dimethyl-4,8-di-tert-butyl-dibenz[d,f][1,3,2]dioxaphosphepin-6-yl)-N,N'-dicycloheptylhexamethylenediamine,

(18) 1,4-bis-(2',4',8',10'-tetra-tert-butyl-dibenz[d,f][1,3,2-]dioxaphosphepin-6'-yl)-2,5-dimethylpiperazine,

(19) 1,4-bis-[N-(2',4',8',10'-tetra-tert-butyl-dibenz[d,f][1,3,2]dioxaphosphin-6'-yl)-aminopropyl]-piperazine,

(20) N,N',N''-tris-(2,4,8,10-tetra-tert-butyl-dibenz[d,f][1,3,2]dioxaphosphepin-6'-yl)-diethylenetriamine,

(21) N,N-bis[3-[N'-(2',4',8',10'-tetra-tert-butyl-dibenz[d,f][1,3,2]dioxaphosphepin-6'-yl)-aminopropyl]-N-(2'',4'',8'',10''-tetra-tert-butyl-dibenz[d,f[[1,3,2]dioxaphosphepin-6''-yl)-amine,

(22) N,N-bis-(2,4,8,10-tetra-tert-butyl-dibenz[d,f][1,3,2-]dioxaphosphepin-6-yl)-N-n-butylamine,

(23) N,N'-bis-(2,4,8,10-tetra-tert-pentyl-dibenz[d,f][1,3,2]dioxaphosphepin-6-yl)-N,N'-diisopropylhydrazine,

(24) N-cyclohexyl-N-(2,4,8,10-tetra-tert-butyl-dibenz[d,f][1,3,2]dioxaphosphepin-6-yl)-aminosuccinic aciddioctyl ester,

(25) R-N-(cyclohexyl)-(CH$_2$)$_3$-N(R)-(CH$_2$)$_3$-N(R)-(CH$_2$)$_3$-N(R)-(CH$_2$)$_3$-N(cyclohexyl)-R, and

(26) R-N(H)-[CH$_2$-CH$_2$-N(R)]$_4$-CH$_2$CH$_2$-N(H)R.

In the formulae 25 and 26, R denotes the group (2,4,8,10-tetra-tert-butyl-dibenz[d,f][1,3,2]dioxaphosphepin-6-yl):

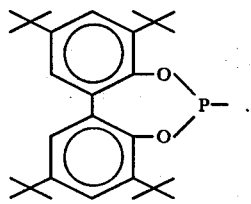

The phosphonites of the formula I can be produced by methods known per se, particularly by amidation or transamidation reactions, for example by reacting a phosphonite of the formula VII

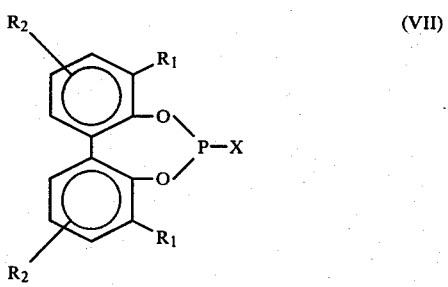

(VII)

wherein X is a reactive group, and R$_1$ and R$_2$ have the meanings given above, with an amine ZA, particularly with an amine of the formula VIII

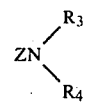

(VIII)

wherein Z is hydrogen or an Na, Li or K atom, and R$_3$ and R$_4$ have the meanings given above.

A reactive group X is for example halogen, particularly chlorine, alkoxy, phenoxy or a primary or secondary amino group.

A further possibility for producing compounds of the formula I is to react a phosphoric acid amide of the formula IX (Hal)$_2$—P—A    (IX)

wherein "Hal" is a halogen atom, especially chlorine, and A has the above-given meaning, with a biphenol of the formula X

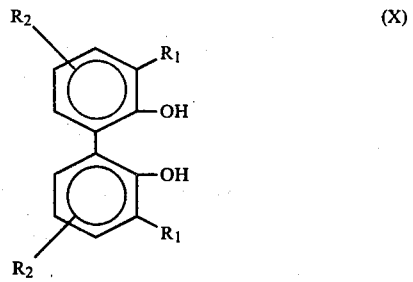

(X)

wherein R$_1$ and R$_2$ have the meanings given above.

Both types of reaction can be performed in a manner known per se, for example between −5° C. and 80° C.; or by heating, preferably to above about 80° C., for example 80°–170° C. The reaction can be performed without, or in the presence of, an inert solvent, such as aprotic solvents, for example ligroin, toluene, xylene, hexane, cyclohexane, dimethylformamide, dimethylacetamide, sulfolane, acetonitrile, dioxane, di-n-butyl ether, 1,2-dichloroethane, dimethylsulfoxide, ethyl acetate, methyl ethyl ketone, nitrobenzene, nitromethane, tetrahydrofuran, chloroform or trichloroethylene. If X is halogen, the reaction is preferably carried out in the presence of a base, such as sodium carbonate, or an amine, for example triethylamine, pyridine or N,N-dimethylaniline. It is however quite possible to perform the reaction with an excess of amine of the formula VIII, with this acting as an acid acceptor. Amine bases used in excess can simultaneously act as solvent.

The starting materials of the formulae VII, VIII, IX and X are known, or, where they are new, they can be produced by methods analogous to known methods. The phosphonites of the formula VI can be produced for example analogously to the method described in Chem. Ber. 89, 1121 (1956).

The compounds of the formula I can be used according to the present invention as stabilisers for plastics and elastomers to protect these from damage caused by the action of oxygen, light and heat. Examples of plastics concerned are the polymers listed in the German Offenlegungsschrift No. 2,456,864 on pages 12–14.

Suitable substrates are for example:

1. Polymers which are derived from monounsaturated hydrocarbons, such as polyolefins, for example low density and high density polyethylene, which can be crosslinked, polypropylene, polyisobutylene, polymethylbut-1-ene and polymethylpent-1-ene.

2. Mixtures of the homopolymers mentioned under 1, for example mixtures of polypropylene and polyethylene, of polypropylene and polybut-1-ene and of polypropylene and polyisobutylene.

3. Copolymers of the monomers on which the homopolymers mentioned under 1 are based, such as ethylene/propylene copolymers, propylene/but-1-ene copolymers, propylene/isobutylene copolymers and ethylene/but-1-ene copolymers, and also terpolymers of ethylene and propylene with a diene, for example hexadiene, di-cyclopentadiene or ethylidenenorbornene.

4. Polystyrene and its copolymers, such as SAN, ABS, IPS, ASA, and EP-modified styrene copolymers.

5. Polyamides.

6. Linear polyesters.

7. Polyurethanes.

8. Polycarbonates.

9. Elastomers, such as polybutadiene, SBR, polyisoprene, polychloroprene and nitrile rubber.

10. Thermoplastic elastomers, such as SBS, SIS and S-EP-S.

11. Polyvinyl chloride, and the like.

12. Lubricating oils having a synthetic or mineral base.

The present invention relates also to a process for stabilising polymers against thermooxidative degradation during production, isolation, processing and use, which process comprises incorporating into the polymer at least one compound of the formula I.

The compounds of the formula I are incorporated into the substrates at a concentration of 0.005 to 5 percent by weight, calculated relative to the material to be stabilised.

Preferably 0.01 to 1.0 percent by weight, and particularly preferably 0.02 to 0.5 percent by weight, of the compounds, relative to the material to be stabilised, is incorporated into this material. Incorporation is effected for example by mixing at least one of the compounds of the formula I, and optionally further additives, by methods customary in the art, into the polymer either before or during shaping, or alternatively by application of the dissolved or dispersed compounds to the polymers, optionally with subsequent removal of the solvent by evaporation.

The new compounds can also be added in the form of a masterbatch, which contains these compounds for example at a concentration of 2.5 to 25 percent by weight, to the plastics to be stabilised.

In the case of crosslinked polyethylene, the compounds are added before crosslinking.

The invention relates therefore also to the plastics which are stabilised by the addition of 0.01 to 5 percent by weight of a compound of the formula I, and which can optionally contain further additives. The plastics stabilised in this manner can be used in the widest variety of forms, for example as films, fibres, tapes or profiles, or as binders for lacquers, adhesives or putties.

Examples of further additives which can be used together with the stabilisers according to the invention are: antioxidants, UV absorbers and light stabilisers, such as 2-(2'-hydroxyphenyl)-benzotriazoles, 2,4-bis-(2'-hydroxyphenyl)-6-alkyl-s-triazines, 2-hydroxybenzophenones, 1,3-bis-(2'-hydroxybenzoyl)-benzenes, esters of substituted or unsubstituted benzoic acids and acrylates, and also nickel compounds, sterically hindered amines, oxalic acid diamides, metal deactivators, phosphites, compounds which destroy peroxide, polyamide stabilisers, basic Co stabilisers, nucleating agents or other additives, for example plasticisers, lubricants, emulsifiers, fillers, carbon black, asbestos, kaolin, talc, glass fibres, pigments, optical brighteners, flameproofing agents and antistatic agents.

The invention is further illustrated by the following Examples.

EXAMPLE 1

(a) A solution of 49.3 ml of piperidine (0.5 mol), 70 ml of triethylamine and 100 ml of toluene is added dropwise to a mixture of 217.5 ml of phosphorus trichloride (2.5 mols) and 200 ml of toluene. The mixture is stirred for one hour at 0°–5° C., and is then held for 10 hours at the reflux temperature. After the reaction has finished, the hydrochloride is removed by filtration, and the residue is subjected to vacuum distillation. The phosphoric acid piperidide chloride boils at 55° C./0.4 mm Hg.

(b) 9.3 g (0.05 mol) of phosphorus acid piperidide dichloride and 20.5 g (0.05 mol) of 4,4',6,6'-tetra-tert-butyl-2,2'-biphenol in 50 ml of triethylamine are refluxed for 20 hours. The hydrochloride is separated and the unreacted triethylamine is removed to leave N-(2,4,8,10-tetra-tert-butyl-dibenz[d,f][1,3,2]dioxaphosphepin-6-yl)-piperidine as an amorphous residue.

| Elementary analysis | | | | |
|---|---|---|---|---|
| calculated: | C 75.68% | H 9.26% | N 2.6% | P 5.9% |
| found: | C 76.2% | H 9.5% | N 2.6% | P 5.8% |

EXAMPLE 2

170 g (0.414 mol) of 4,4',6,6'-tetra-tert-butyl-2,2'-biphenol in 150 ml of toluene is heated to 80°–90° C. in a nitrogen atmosphere, and 40 ml (0.458 mol) of phosphorus trichloride is added dropwise in the course of 2 hours. The reaction mixture is stirred at reflux temperature for 4 hours and, towards the end of the reaction, nitrogen gas is again introduced. There is then added dropwise at reflux temperature, during 1½ hours, a solution of 53.5 g (0.414 mol) of dibutylamine and 41.9 g (0.414 mol) of triethylamine in 80 ml of toluene. After 15 hours, the reaction mixture is allowed to cool to room temperature, and the triethylamine hydrochloride which has precipitated is filtered off. The toluene is afterwards evaporated off, and the N-(2,4,8,10-tetra-tert-butyl-dibenz[d,f][1,3,2]dioxaphosphepin-6-yl)-dibutylamine obtained has a melting point of 140° C.

EXAMPLE 2a

By a procedure analogous to that described in Example 2, by substituting dibutylamine with hexamethyleneimine, N-(2,4,8,10-tetra-tert.-butyl-dibenz[d,f][1,3,2]-dioxaphosphepin-6-yl)-hexamethyleneimine is obtained which has a melting point of 164°–165° C.

EXAMPLES 3–10

170 g (0.414 mol) of 4,4',6,6'-tetra-tert-butyl-2,2'-bisphenol and 36.1 ml of phosphorus trichloride in 150 ml of xylene are heated to 110°–115° C. After 4 hours, there is added dropwise to the reaction mixture, in the course of 1.5 hours, a solution of 36.1 g (0.414 mol) of morpholine and 58 ml of triethylamine in 80 ml of xylene, and stirring is maintained for a further 20 hours at 110°–120° C. The triethylamino hydrochloride is then filtered off, and the solvent is filtered off in vacuo to leave the product, N-(2,4,8,10-tetra-tert-butyl-dibenz[d,f][1,2,3]dioxaphosphepin-6-yl)-morpholine, as a crystalline residue (m.p. 140°–143° C.).

The following products are obtained by a procedure analogous to that described in Example 3.

| No. | Formula | | Melting point | |
|---|---|---|---|---|
| 4 | N-(2,4,8,10-tetra-tert-butyl-dibenz[d,f][1,3,2]dioxaphosphepin-6-yl)-diisopropylamine | | 189° C. | |
| 5 | N-(2,4,8,10-tert-butyl-dibenz[d,f][1,3,2]dioxaphosphepin-6-yl)-dicyclohexylamine | | 270° C. | |
| 6 | N-(4,8-di-tert-butyl-2,10-di-tert-octyl-dibenz[d,f]-[1,3,2]dioxaphosphepin-6-yl)-morpholine | | 131–134° C. | |
| 7 | N,N'-di-(2,4,8,10-tetra-tert-butyl-dibenz[d,f][1,3,2]dioxaphosphepin-6-yl)-piperazine | | 260° C. | |
| 8 | N-(2,4,8,10-tetra-tert-butyl-dibenz[d,f][1,3,2]dioxaphosphepin-6-yl)-p-dodecyl-phenylamine | cal. found | Characteristics oil P 4.42% P 3.57% | N 2.00% N 1.8% |
| 9 | N,N-di-(2,48,10-tetra-tert-butyl-dibenz[d,f][1,3,2]dioxaphosphepin-6-yl)-ethylenediamine | | 260° C. | |
| 10 | N-(2,4,8,10-tetra-tert-octyl-dibenz[d,f][1,3,2]dioxaphosphepin-6-yl)-dibutylamine | | oil | |

EXAMPLE 11

100 parts of high-density polyethylene having a molecular weight of about 500,000 ("Lupolen 5260 Z" in powder form, BASF) containing 0.05 part of pentaerithritol-tetra-[3,5-di-tert-butyl-4-hydroxyphenyl)-propionate] are mixed dry with 0.1 part of each of the phosphonites shown in Table 1 below. The mixtures are kneaded in a Brabender plastograph at 220° C. at 50 r.p.m. During this time, the kneading resistance is continuously recorded as a turning moment. As a result of crosslinking of the polymer, there occurs in the course of kneading a rapid increase in the turning moment after an initial period of constant value. The effectiveness of the stabilisers is manifested by a lengthening of the time in which this value remains constant.

TABLE 1

| Parts of phosphonite | Time in minutes until the turning moment changes |
|---|---|
| none | 3 |
| 0.1 part of compound 1 | 17.5 |
| 0.1 part of compound 4 | 13.5 |
| 0.1 part of compound 5 | 9.5 |
| 0.1 part of compound 2a | 18 |

What is claimed is:

1. N-(2,4,8,10-tetra-tert.butyldibenz[d,f][1,3,2]dioxaphosphepin-6-yl)-hexamethyleneimine.

2. A stabilised organic polymer containing from 0.005 to 5% by weight of a compound according to claim 1.

3. Stabilised organic polymer according to claim 2, which is a polyolefin.

* * * * *